US007390489B2

(12) United States Patent
Youn et al.

(10) Patent No.: US 7,390,489 B2
(45) Date of Patent: Jun. 24, 2008

(54) MONOCLONAL ANTIBODY SELECTIVELY RECOGNIZING LISTERIA MONOCYTOGENES, HYBRIDOMA PRODUCING THE ANTIBODY, TEST KIT COMPRISING THE ANTIBODY AND DETECTION METHOD OF LISTERIA MONOCYTOGENES USING THE ANTIBODY

(75) Inventors: Byung Soo Youn, Seoul (KR); Young Soo Yang, Seoul (KR); Nam Seok Lee, Seoul (KR); Kang Yeol Yu, Jeonju-si (KR); Young Soon Noh, Seoul (KR); Hong Je Park, Seoul (KR); Moon Yeon Youn, Seoul (KR); Min Sup Chung, Seoul (KR); Sung Shik Min, Seoul (KR); Jae Jun Jeong, Busan (KR)

(73) Assignee: Komed Co., Ltd. (KR)

( * ) Notice: Subject to any disclaimer, the term of this patent is extended or adjusted under 35 U.S.C. 154(b) by 514 days.

(21) Appl. No.: 10/961,274

(22) Filed: Oct. 8, 2004

(65) Prior Publication Data
US 2006/0078951 A1    Apr. 13, 2006

(51) Int. Cl.
*A61K 39/395* (2006.01)
*A61K 39/00* (2006.01)
*A61K 39/40* (2006.01)
*G01N 33/53* (2006.01)
*G01N 33/554* (2006.01)
*G01N 33/569* (2006.01)

(52) U.S. Cl. ............... 424/139.1; 424/130.1; 424/133.1; 424/135.1; 424/141.1; 424/143.1; 424/150.1; 424/156.1; 424/164.1; 436/547; 436/548; 435/7.1; 435/7.2; 435/7.32; 435/7.92; 435/7.94; 435/34; 435/39; 435/70.21; 435/243; 530/388.1; 530/388.2; 530/388.4; 530/391.1

(58) Field of Classification Search .............. 424/130.1, 424/136.1, 139.1, 141.1, 133.1, 135.1, 143.1, 424/150.1, 156.1, 164.1, 178.1; 435/41, 435/70.21, 7.1, 7.2, 7.32, 7.92, 7.94, 34, 435/39, 243; 530/388.1, 388.2, 388.4, 388.85, 530/391.1; 436/547, 548
See application file for complete search history.

(56) References Cited

U.S. PATENT DOCUMENTS

| | | | | |
|---|---|---|---|---|
| 3,817,837 | A | 6/1974 | Rubenstein et al. | 195/103.5 |
| 3,850,752 | A | 11/1974 | Schuurs et al. | 195/103.5 |
| 3,939,350 | A | 2/1976 | Kronick et al. | 250/365 |
| 3,996,345 | A | 12/1976 | Ullman et al. | 424/12 |

(Continued)

FOREIGN PATENT DOCUMENTS

| | | |
|---|---|---|
| JP | 06233699 | 8/1994 |
| JP | 08143598 | 6/1996 |

OTHER PUBLICATIONS

Choi et al. 2001. Biotechnology Letter. vol. 23: 1669-1673.*
Japanese Office Action mailed Jun. 20, 2007 for Application No. 2004-295072 (All references cited in Office Action are listed above).

*Primary Examiner*—Mark Navarro
*Assistant Examiner*—JaNa Hines
(74) *Attorney, Agent, or Firm*—Cantor Colburn LLP

(57) ABSTRACT

The present invention relates to a monoclonal antibody binding specifically to the p60 protein of *Listeria monocytogenes*, a hybridoma cell producing the monoclonal antibody, a test kit comprising the monoclonal antibody, and a method for detecting *Listeria monocytogenes* using the monoclonal antibody. The inventive monoclonal selectively recognizes only *Listeria monocytogenes*, so that the use of such an antibody allows for rapid determination of the food contamination with these bacteria pathogenic to humans.

8 Claims, 8 Drawing Sheets

U.S. PATENT DOCUMENTS

| | | | |
|---|---|---|---|
| 4,275,149 A | 6/1981 | Litman et al. | 435/7 |
| 4,277,437 A | 7/1981 | Maggio | 422/61 |
| 4,366,241 A | 12/1982 | Tom et al. | 435/7 |
| 5,294,537 A * | 3/1994 | Batt | 435/7.32 |

* cited by examiner

[figure 1a]
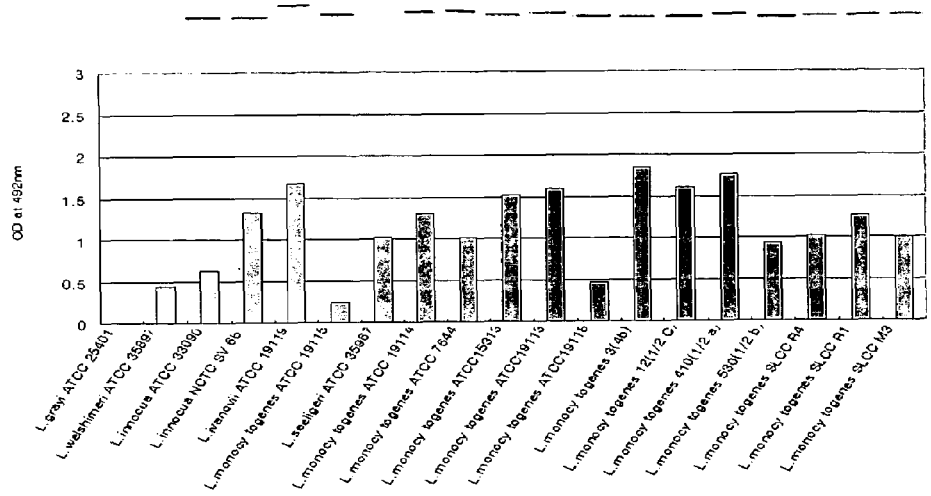
[figure 1b]
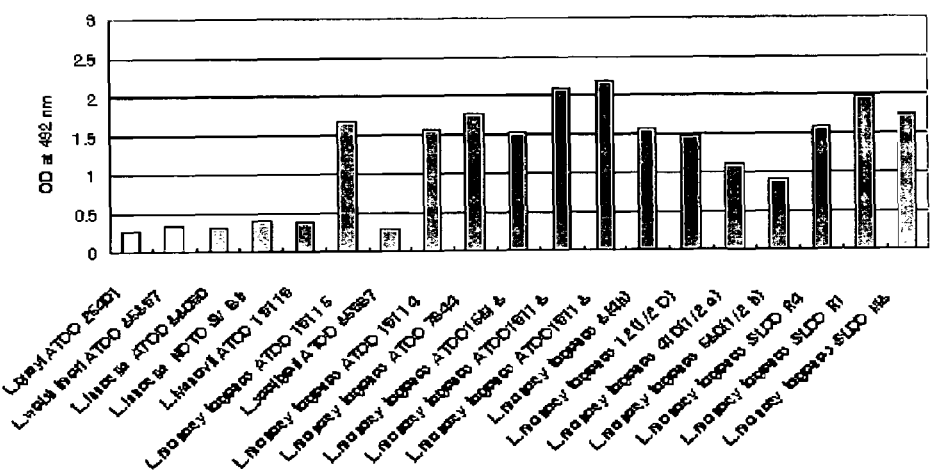

[figure 1c]
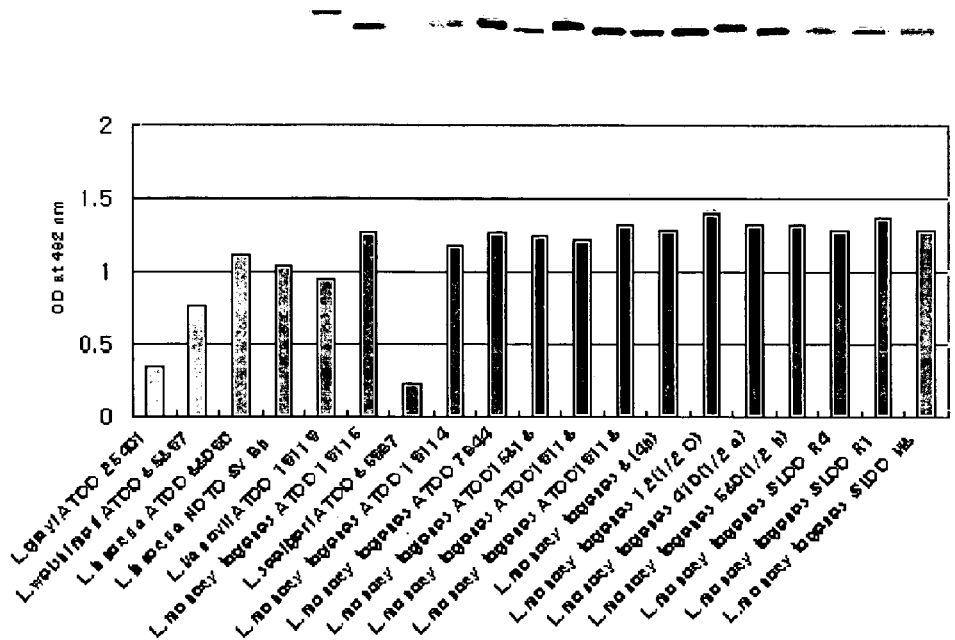
[figure 2a]
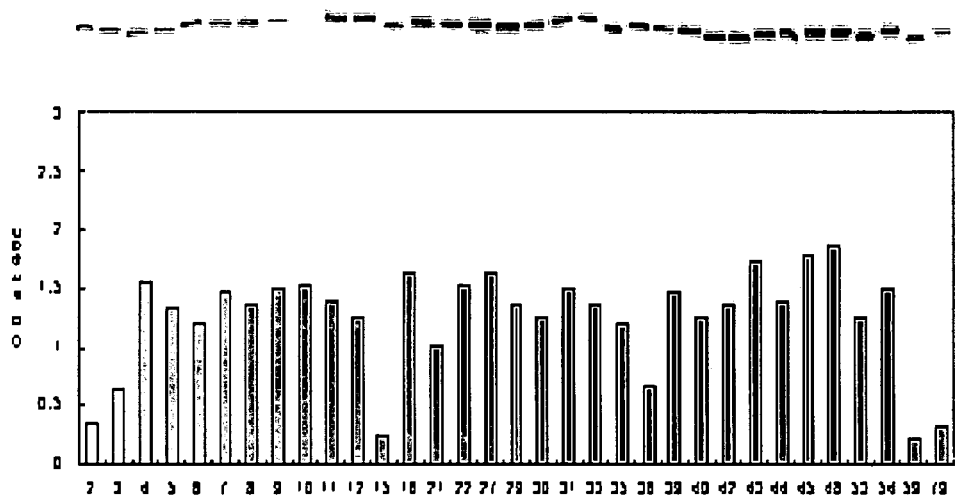

[figure 2b]
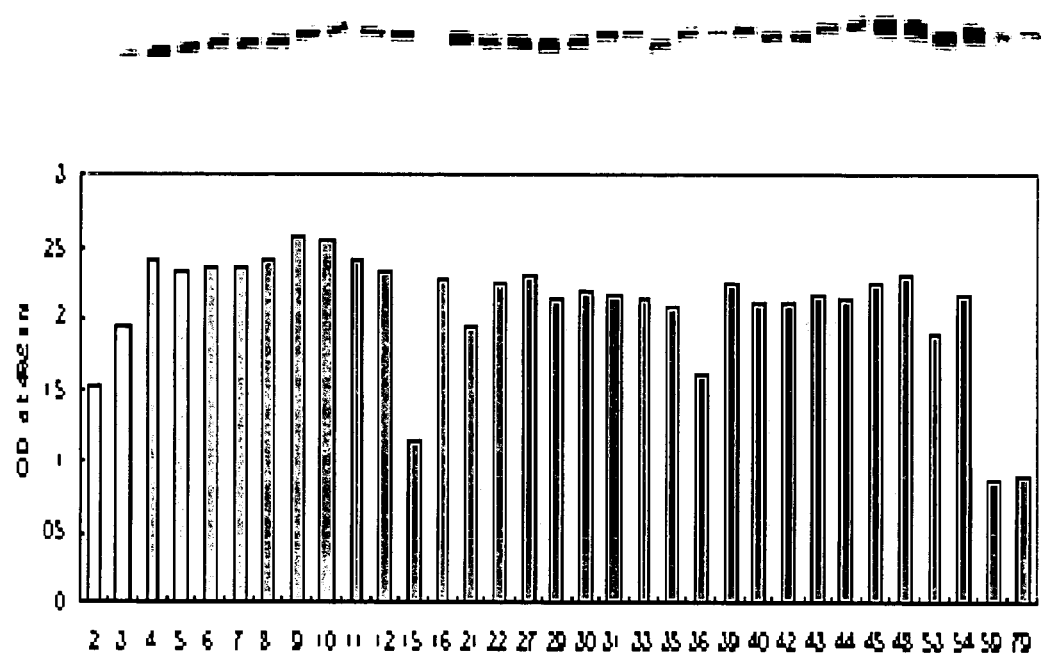

[figure 2c]
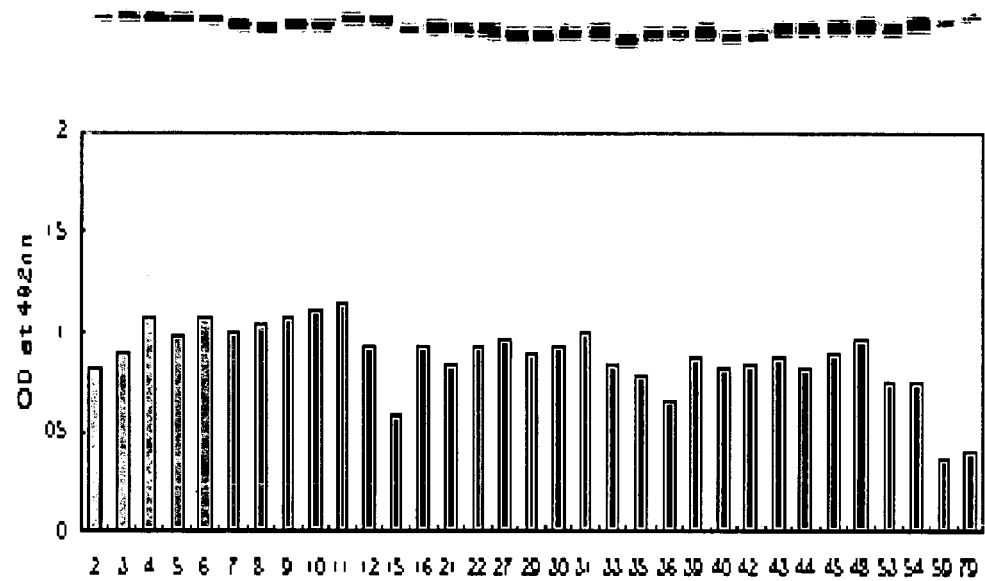
[figure 3a]
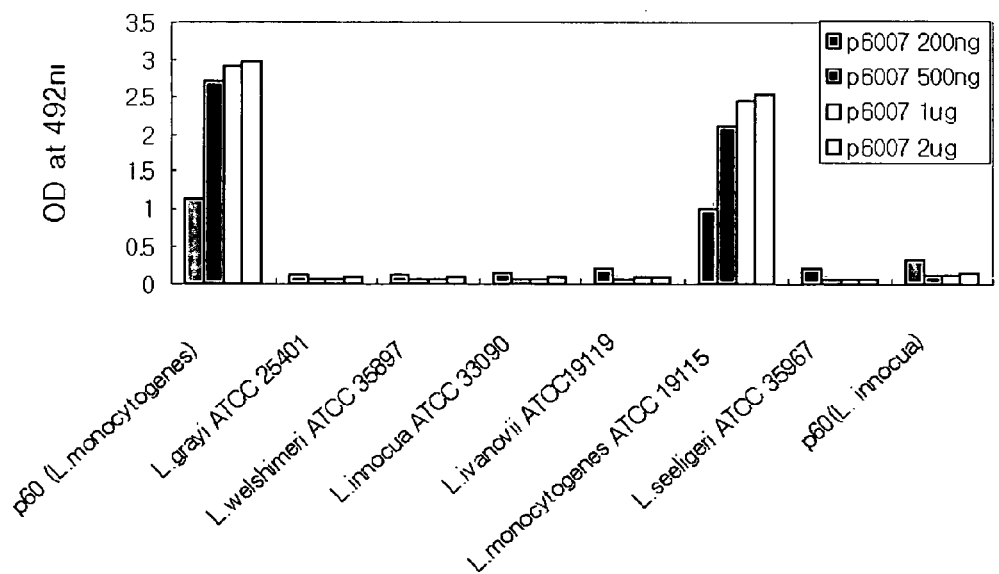

[figure 3b]
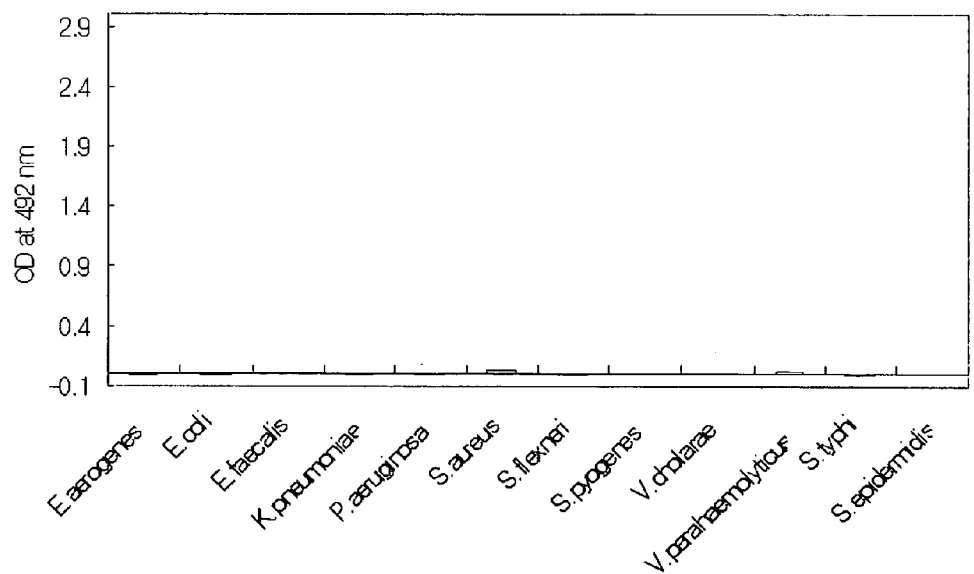
[figure 4a]
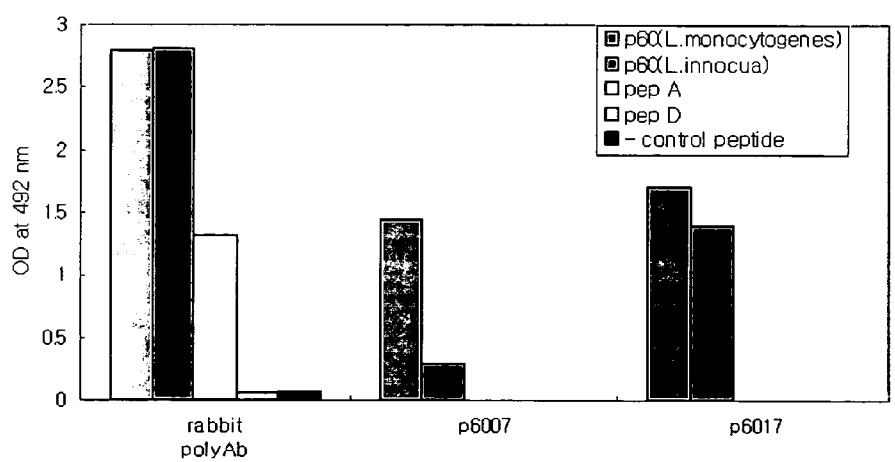

[figure 4b]
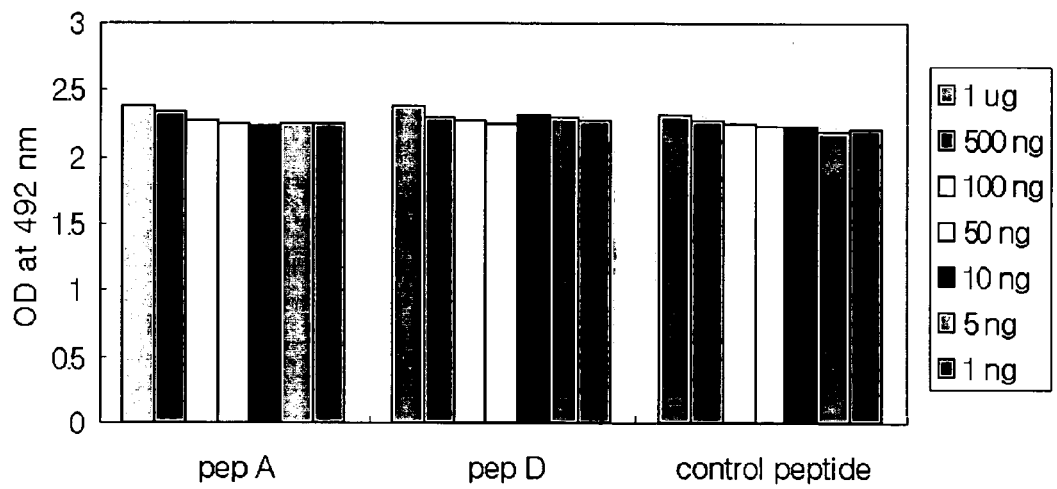
[figure 4c]
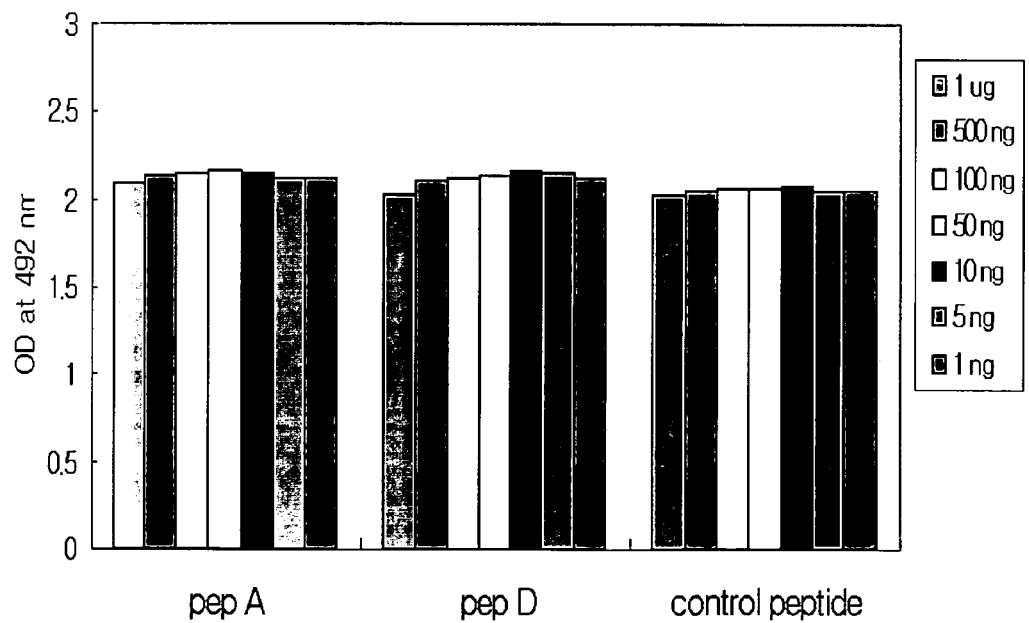

【figure 5a】

| | 1 | 2 | 3 | 4 | 5 | 6 | 7 | 8 |
|---|---|---|---|---|---|---|---|---|
| ng | 1000 | 500 | 250 | 125 | 60 | 30 | 15 | - |

| 0 | 1 | 2 | 3 | 4 | 5 | 6 | 7 | 8 | 9 | 10 | 11 | 12 |
|---|---|---|---|---|---|---|---|---|---|---|---|---|

C(control)

T(test)

[figure 6a]
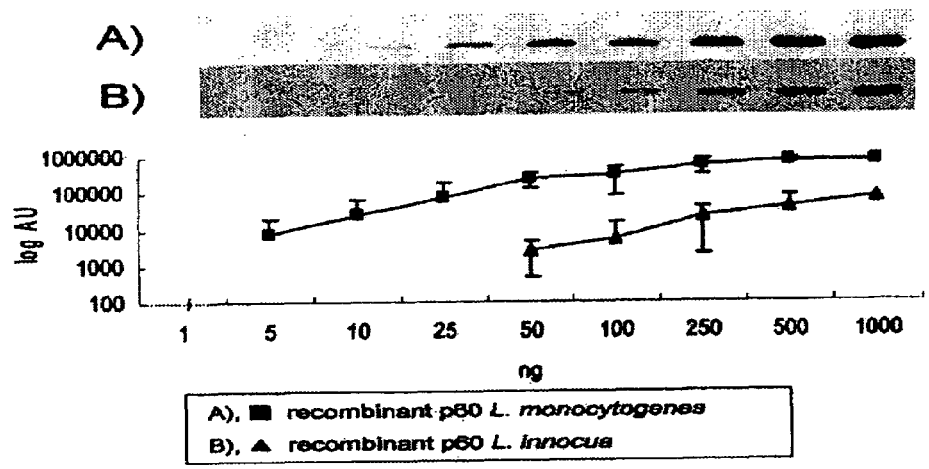
[figure 6b]
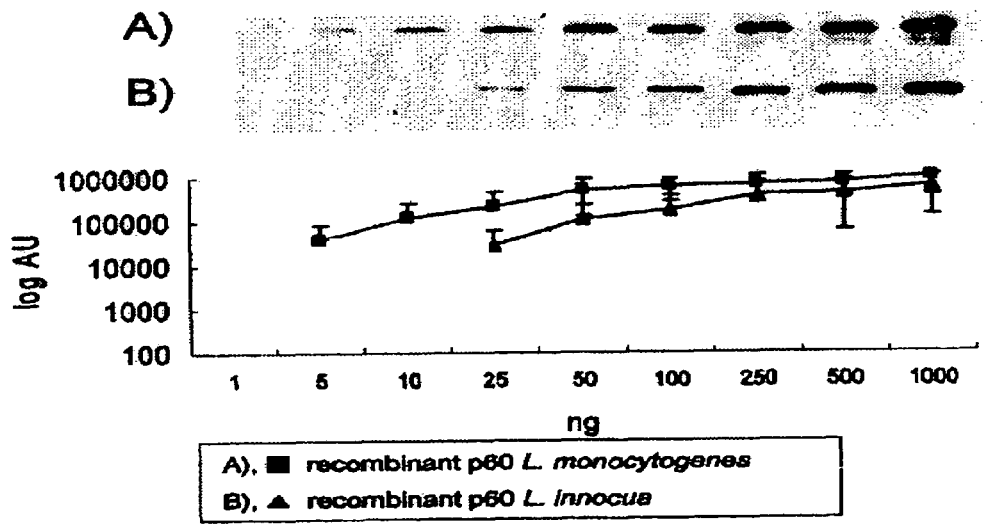

MONOCLONAL ANTIBODY SELECTIVELY RECOGNIZING LISTERIA MONOCYTOGENES, HYBRIDOMA PRODUCING THE ANTIBODY, TEST KIT COMPRISING THE ANTIBODY AND DETECTION METHOD OF LISTERIA MONOCYTOGENES USING THE ANTIBODY

BACKGROUND OF THE INVENTION

1. Field of the Invention

The present invention relates to rapid determination of the infection and food contamination with *Listeria monocytogenes*, and more particularly to a monoclonal antibody binding specifically to the p60 protein of *Listeria monocytogenes*, a hybridoma cell producing the monoclonal antibody, a test kit comprising the monoclonal antibody, and a method for detecting *Listeria monocytogenes* using the monoclonal antibody.

2. Background of the Related Art

*Listeria* species are Gram-positive, facultative rods which are widely distributed in the natural environment. *Listeria* spp. includes *Listeria monocytogenes, Listeria ivanovii, Listeria innocua, Listeria seeligeri, Listeria welshimeri* and *Listeria grayi*. Among them, only *Listeria monocytogenes* is pathogenic to humans, and strains pathogenic to animals are *Listeria monocytogenes* and *Listeria ivanovii*. Particularly, if *Listeria monocytogenes* contaminates food requiring cold storage, it can survive and proliferate in the low-temperature storage process for a long time period so that it becomes an important *bacillus* causing food poisoning mediated by cold storage food. Furthermore, if listeriosis caused by this *bacillus* becomes serious, it will cause septicemia and meningitis and induce miscarriage of pregnant women. *Listeria monocytogenes* is particularly hazardous to infants, very old persons, pregnant women and immune deficient patients, and shows a high death rate reaching 30% in patients with listeriosis. This listeriosis is known to be caused mainly by foods, such as meat, meat processing products, vegetables, and milk processing products. Thus, rapid diagnosis of the food contamination with *Listeria monocytogenes* is necessary for the prevention of listeriosis.

*Listeria* identification methods which can be currently used in hospitals, industries (food companies, meat companies and milk processing companies) and the like include various conventional methods using biochemical assays, but they are inefficient methods requiring much time and labor.

Diagnostic methods which are used for the rapid determination of the infection and food contamination with *Listeria monocytogenes* include molecular biological methods, such as polymerase chain reaction (PCR), but such methods are unsuitable for actual clinical and industrial applications due to limitations in technical capabilities and accuracies. Moreover, immunological methods such as enzyme immunoassay (EIA) are frequently used, but show non-specificity, which leads to inaccurate test results or makes additional verification tests necessary.

Kits known to be used for the rapid detection of *Listeria* bacteria include non-radioactive DNA probe kits using PCR techniques and nucleic acid hybridization assays, and kits using immunoassays. Furthermore, there are kit products developed for a dipstick assay using immunochromatography. However, all the kits have a disadvantage in that they either cannot specifically detect only *Listeria monocytogenes* or detect all *Listeria* species.

Since it was difficult to produce a monoclonal antibody to *Listeria monocytogenes*, an ELISA or dipstick detection kit with a monoclonal antibody which selectively recognizes this bacterial strain could not be developed. This is because either the whole *Listeria monocytogenes* strain was used as an antigen, or even when certain antigens were used, a monoclonal antibody specific only to *Listeria monocytogenes* was not produced.

Murein hydrolase p60 proteins which exist commonly in *Listeria* spp. are exo enzymes that *Listeria* secretes for cell division. Prior to the present invention, polyclonal antibodies were produced using certain peptides of p60, for example, pepA and pepD (Bubert A. et al., Appl. Environ Microbiol, 60(9), 3120-7, 1994). However, such polyclonal antibodies showed weak effects due to their low titer and the unsuitable application of a sandwich ELISA system, so that they were insufficient for commercial use. The present inventors have produced a new monoclonal antibody which can selectively recognize *Listeria monocytogenes* whose putative epitope may differ from the pepA or pepD peptide region of p60 that has been described somewhere (Example 4 and FIG. 4a).

Under this background, the present inventors have produce a monoclonal antibody recognizing a specific epitope of *Listeria monocytogenes* p60 proteins, among murein hydrolase p60 proteins which exist commonly in *Listeria* genus.

SUMMARY OF THE INVENTION

In one aspect, the present invention provides a monoclonal antibody binding specifically to the p60 protein of *Listeria monocytogenes*, which is produced by a hybridoma cell of Accession Number KCTC 10431BP, as well as a monoclonal antibody binding specifically to the p60 protein of *Listeria* spp., which is produced by a hybridoma cell of Accession Number KCTC 10432BP.

In another aspect, the present invention provides hybridoma cells producing said monoclonal antibodies.

In still another aspect, the present invention provides a test kit for detecting *Listeria monocytogenes* contamination, which comprises a monoclonal antibody binding specifically to the p60 protein of *Listeria monocytogenes*.

The test kit is preferably an ELISA kit or a dipstick kit using immunochromatography.

In the test kit, a second antibody binding to an antigen captured by the monoclonal antibody binding specifically to the p60 protein of *Listeria monocytogenes* is preferably a monoclonal antibody binding specifically to the p60 protein of *Listeria* spp.

In further another aspect, the present invention provides a method for detecting *Listeria monocytogenes* contamination, which comprises contacting a test sample with a monoclonal antibody binding specifically to the p60 protein of *Listeria monocytogenes*, and determining the presence of an antigen-antibody complex between the p60 protein of *Listeria monocytogenes* and the monoclonal antibody.

In the detection method, the antigen-antibody complex is preferably detected by an RIA, ELISA, immunofluorescence, particle agglutination, or chemiluminescence assay.

In the detection method, a second antibody binding to an antigen captured by the monoclonal antibody binding specifically to the p60 protein of *Listeria monocytogenes* is preferably a monoclonal antibody binding specifically to the p60 protein of *Listeria* spp.

BRIEF DESCRIPTION OF THE DRAWINGS

FIG. 1*a* is a graphic diagram showing the results of direct ELISA and Western blot tests using a polyclonal antibody (rabbit) for a variety of *Listeria* spp.

FIG. 1b is a graphic diagram showing the results of sandwich ELISA and Western blot tests using monoclonal antibody p6007 for a variety of *Listeria* spp.

FIG. 1c is a graphic diagram showing the results of sandwich ELISA and Western blot tests using monoclonal antibody p6017 for a variety of *Listeria* spp.

FIG. 2a is a graphic diagram showing the results of direct ELISA and Western tests using a polyclonal antibody (rabbit) for 33 *Listeria monocytogenes* strains isolated from food.

FIG. 2b is a graphic diagram showing the results of direct ELISA and Western tests using monoclonal antibody p6007 for 33 *Listeria monocytogenes* isolated from food.

FIG. 2c is a graphic diagram showing the results of direct ELISA and Western tests using monoclonal antibody p6017 for 33 *Listeria monocytogenes* strains isolated from food.

FIG. 3a is a graphic diagram showing the results of ELISA tests with varying amounts of monoclonal antibody p6007 for *Listeria* spp.

FIG. 3b is a graphic diagram showing the results of sandwich ELISA using monoclonal antibody p6007 for other bacterial strains than *Listeria* strains.

FIG. 4a is a graphic diagram showing the results of direct ELISA tests in the presence of competitors on whether pepA and pepD peptides are recognized by a polyclonal antibody, monoclonal antibody p6007 and monoclonal antibody p6017.

FIG. 4b is a graphic diagram showing the results of ELISA assays using monoclonal antibody p6007 as a capture antibody and a polyclonal antibody as a second antibody in order to examine the competition between pepA and pepD peptides.

FIG. 4c is a graphic diagram showing the results of sandwich ELISA assays using monoclonal antibody p6007 as a capture antibody and monoclonal antibody p6017 as a second antibody in order to examine the competition between pepA and pepD peptides.

FIGS. 5a and 5b are photographs showing *Listeria* deepstick deployments of recombinant p60 from *L. monocytogenes* using immunity chromatography.

FIGS. 6a and 6b are graphic diagrams showing a set of binding kinetics assays and Western blot analysis for comparison of binding characteristics between p6007 and p6017 as different concentrations of recombinant p60 of *L. monocytogenes* and *L. innocua*.

DETAILED DESCRIPTION OF THE PREFERRED EMBODIMENT

The present invention relates to a monoclonal antibody specifically detecting *Listeria monocytogenes*.

In one aspect, the present invention relates to a monoclonal antibody binding specifically to the p60 protein of *Listeria monocytogenes*, the antibody being produced by a hybridoma cell of Accession Number KCTC 10431BP.

In another aspect, the present invention relates to a monoclonal antibody binding specifically to the p60 protein of *Listeria* spp., the antibody being produced by a hybridoma cell of Accession Number KCTC 10432BP.

As used herein, the term "monoclonal antibody" which is well known in the art refers to a highly specific antibody directed against a single antigenic site. Generally, unlike polyclonal antibodies including different antibodies directed against different epitopes, the monoclonal antibody has an advantage in that it improves the selectivity and specificity of diagnostic and analytical assays using antigen-antibody bonding. Another advantage is that the monoclonal antibody is not contaminated with other immunoglobulins since it is synthesized by hybridoma culture.

The monoclonal antibody according to the present invention is prepared by immunizing animals with p60 as an immunogen, fusing the spleen cells of the immunized animals with myeloma cells so as to produce hybridomas, selecting a hybridoma binding specifically to the p60 protein of *Listeria monocytogenes*, and producing the monoclonal antibody from the selected hybriddoma.

In an embodiment of the present invention, a recombinant p60 protein was used as an immunogen in the preparation of the monoclonal antibody. This recombinant p60 protein was prepared by amplifying a known base sequence (Andreas B., et al., J. Bacteriol., 174: 8166-8171, 1992) by PCR according to a method known in the art, inserting the PCR-amplified product into a pET-21a vector, and expressing and purifying the recombinant vector *Escherichia coli*. Mice were immunized with the recombinant p60 protein as an immunogen, and spleen cells from the immunized mice isolated and fused with myeloma cell P3X63Ag8.653. By ELISA and Western blot tests, hybridomas having a high antibody activity against the p60 protein were selected, and the selected hybridomas were cultured again. From the cultured hybridomas, positive hybridomas p6007 and 6017 were selected by ELISA and Western blot tests. The results of ELISA and Western blot tests for the culture supernatant of the hybridomas showed that only the hybridoma p6007 selectively recognized *Listeria monocytogenes*. The selected hybridomas were injected into the abdominal cavity of animals, and after a given time period, ascites from the animals were collected from which monoclonal antibodies were isolated.

Each of the purified monoclonal antibodies was identified by sandwich ELISA, direct ELISA and Western blot tests. As used herein, "monoclonal antibody p6007" refers to a monoclonal antibody secreted by hybridoma p6007, and the term "monoclonal antibody p60017" refers to a monoclonal antibody secreted by hybridoma p6017.

From the results of the sandwich ELISA and Western blot tests, the monoclonal antibody p6007 was identified as a monoclonal antibody selectively recognizing only *Listeria monocytogenes*, and the monoclonal antibody p6017 was identified as a monoclonal antibody selectively recognizing *Listeria* spp. (FIG. 1).

As described above, the monoclonal antibody p6007 found to selectively recognize only *Listeria monocytogenes*, and the monoclonal antibody p6017 found to selectively recognize *Listeria* spp., selectively recognized all of 33 *Listeria monocytogenes* strains isolated from food (FIGS. 2b and 2c).

Furthermore, whether the inventive monoclonal antibodies p6007 and p6017 would recognize pepA and pepD peptides or not was tested by direct ELISA. The inventive monoclonal antibodies p6007 and p6017 were not bound to pepA and pepD, thus indicating that the inventive monoclonal antibodies do not utilize the epitopes of pepA and pepD (FIG. 4a). Even when the competition between pepA and pepD was tested by sandwich ELISA, the monoclonal antibody p6007 showed saturated OD values without a difference in OD values with a change in the addition amounts of pepA and pepD, even though OD values must be changed with a change in the addition amounts of pepA and pepD if the monoclonal antibody p6007 utilizes the epitopes of pepA and pepD. This suggests that the monoclonal antibody p6007 do not utilize the epitopes of pepA and pepD (FIGS. 4b and 4c).

The hybridoma p6007 producing the inventive monoclonal antibody p6007 selectively recognizing *Listeria monocytogenes* was deposited under accession number KCTC 10431BP on Feb. 21, 2003 with the Korean Collection for Type Cultures (KCTC). The hybridoma p6017 producing the inventive monoclonal antibody p6017 selectively recognizing *Listeria* spp. was deposited under accession number KCTC 10432BP on Feb. 21, 2003 with the Korean Collection for Type Cultures (KCTC).

Accordingly, in another aspect, the present invention relates to hybridoma p6007 (KCTC 10431BP) producing the monoclonal antibody p6007. Also, the present invention relates to hybridoma p6017 (KCTC 10432BP) producing the monoclonal antibody p6017.

The inventive monoclonal antibody p6007 has high specificity and sensitivity to *Listeria monocytogenes*, in addition to reactivity with epitopes accessible by immunological assays of the standard strains. Thus, the monoclonal antibody p6007 is suitable for the specific detection of *Listeria monocytogenes*.

As used herein, the term "antigen-antibody complex" means a combination of a p60 protein antigen for determining the presence or absence of *Listeria monocytogenes* in a sample and a monoclonal antibody recognizing the protein antigen.

In the inventive detection method, a culture supernatant heated for 5 to 15 minutes is used as a test sample.

The detection of an antigen-antibody complex between the inventive monoclonal antibody p6007 and *Listeria monocytogenes* may be performed by any known methods, such as spectrophotometric, photochemical, biochemical, immunochemical, electrical, light-absorbing, chemical, or other methods.

For the purpose of the present invention, the detection of the antigen-antibody complex may preferably be performed by an RIA, ELISA, immunofluorescence, particle agglutination, or chemiluminescence assay.

The detection of the antigen-antibody complex involves the use of a directly or indirectly labeled antibody, and examples of detection markers which can be used in the present invention include biotin-streptoavidin conjugates, fluorescent dyes (e.g., fluorescein, Texas red, rhodamine, green fluorescent protein, etc.), radioactive markers (e.g., $^3$H, $^{125}$I, $^{35}$S, $^{14}$C or $^{32}$P), enzymes (e.g., HRP, alkaline phosphatase and other enzymes which are generally used in ELISA), and color markers, such as colloidal gold or color glass or plastic (e.g., polystyrene, polypropylene, latex, etc) beads. The use of such markers is described in U.S. Pat. Nos. 3,817,837, 3,850,752, 3,939,350, 3,996,345, 4,277,437, 4,275,149, and 4,366,241, and Handbook of Fluorescent Probes and Research Chemicals (6th Ed., Molecular Probes, Inc., Eugene Oreg.), which are incorporated by reference herein.

ELISA is particularly preferable for the detection of the antigen-antibody complex in the present invention. According to the ELISA detection method, a test sample is contacted with the inventive monoclonal antibody coated on a solid support, such as a microtiter plate, a membrane, a test strip, or the like. In a concrete embodiment, microtiter plate wells are coated with the inventive monoclonal antibodies, and the nonoccupied region of the wells are blocked with, for example, BSA. Next, the coated plate wells are incubated with the test sample, and then, the presence or absence of an antigen-antibody complex can be determined. The presence of the antigen-antibody complex may be detected using antigen-specific antibodies, for example monoclonal or polyclonal antibodies binding specifically to the p60 protein of *Listeria monocytogenes*, or monoclonal or polyclonal antibodies binding specifically to the p60 protein of *Listeria* spp. The monoclonal or polyclonal antibodies may have a detection market, and if they have no detection marker, their presence can be detected by treatment with a second antibody capable of detecting these monoclonal or polyclonal antibodies.

In the inventive detection method, the second antibody binding to an antigen bound to the polyclonal antibody p6007 selectively recognizing *Listeria monocytogenes* is preferably a monoclonal antibody selectively recognizing *Listeria* spp. The p6017 monoclonal antibody is particularly preferable.

In one illustration, *Listeria monocytogenes* may be detected by reacting the monoclonal antibody p6007 with a sample, binding to the sample the monoclonal antibody p6017 binding specifically to the p60 protein of *Listeria* spp., and measuring the signal of the detection marker. Alternatively, *Listeria monocytogenes* may be detected by adding to the antigen-antibody complex an antibody having a marker capable of producing a detectable signal, and measuring the signal of the detection marker.

Moreover, another method which is particularly preferable for the detection of the antigen-antibody complex in the present invention includes a gold particle conjugation method of conjugating the monoclonal antibody to colloidal gold particle.

In still another aspect, the present invention relates to a test kit for detecting *Listeria monocytogenes*, which comprises the monoclonal antibody p6007 binding specifically to the p60 protein of *Listeria monocytogenes*.

The monoclonal antibody which is used in the inventive test kit for detecting *Listeria monocytogenes* may also be a fragment of the monoclonal antibody as long as the fragment can selectively recognize *Listeria monocytogenes*. Examples of such an antibody fragment may include F(ab')2, Fab, Fab', and Fv fragments.

The inventive test kit for detecting *Listeria monocytogenes* may comprise not only the monoclonal antibody p6007 or its fragment selectively recognizing *Listeria monocytogenes*, but also tools/reagents used in immunological analysis.

The tools/reagents used in immunological analysis include a suitable carrier, a marker capable of producing detectable signals, a lytic agent, and a cleaning agent. In addition, if the marker is enzyme, the kit may comprise a substrate capable of measuring enzymatic activity, and a reaction terminator.

Examples of a suitable carrier include, but are not limited to, soluble carriers, for example, physiologically acceptable buffer solution known in the art (e.g., PBS), insoluble carriers, for example, polymers, such as polystyrene, polyethylene, polypropylene, polyester, polyacrylonitrile, fluorine resin, and magnetic microparticle of metal plated on latex, paper, glass, metal, agarose, and combinations thereof.

Assay systems for use in the inventive detection method and kit include, but are not limited to, ELISA plates, dipstick devices, immunochromatography test strips, radioimmunoassay devices, and flow-through devices.

The inventive test kit for detecting *Listeria monocytogenes* is preferably an ELISA kit or a dipstick using immunochromatography.

In the inventive test kit, the second antibody binding to an antigen bound to the monoclonal antibody p6007 selectively recognizing *Listeria monocytogenes* may preferably be a monoclonal antibody selectively recognizing *Listeria* spp. Particularly preferable is monoclonal antibody p6017.

Hereinafter, the present invention will be described in further detail by the following examples. It is to be understood, however, that these examples are given for illustrative purpose only and not intended to limit the scope of the present invention.

EXAMPLES

Example 1

PCR and Cloning

In order to clone the invasion-associated protein (iap) gene of p60 protein of *Listeria monocytogenes* (Andreas, B. et al., J. Bacteriol., 174: 8166-8171, 1992), the gene was first amplified by PCR.

Primers, i.e., iap-F-pET (5'-GGG AAT TCC ATA TGA GCA CTG TAG TAG TCG AAG CT-3') (SEQ ID NO: 1) and iap-R-pET (5'-GCC GCT CGA GTA CGC GAC CGA AGC CAA C-3') (SEQ ID NO: 2), were so designed that all regions except for a signal sequence were included and also a stop codon was excluded according to the characteristics of a pET-21a vector. Furthermore, for cloning, NdeI was added to the forward primer, and an XhoI restriction site to the reverse primer. PCR was performed in a total volume of 50 μl using 10 ng of the chromosomal DNA of *Listeria monocytogenes*, 5 μl of 10×fu buffer (Stratagene), 1U cloned Pfu polymerase, 0.2 mM dNTP, and 10 pmol of each of the primers. For higher fidelity, Pfu polymerase (Stratagene) was used. The PCR reaction was performed using PTC-150 (MJ Research) for 30 cycles each consisting of 1 minute at 94° C., 1 minute at 55° C., and 2 minutes 72° C.

After completion of the PCR reaction, the PCR product was purified using a PCR purification kit (QIAQUICK™, Qiagen). For cloning, the purified DNA was treated with restriction enzymes NdeI and XhoI (New England Biolabs, Inc.) in NEB buffer 4 (New England Biolabs, Inc.). After restriction enzyme treatment, the DNA was electrophoresed on 1% agarose gel and purified with a spin kit (GENECLEAN®, Q-BIO gene). The purified DNA was bound to a NdeI- and XhoI-treated pET-21a vector by T4 DNA ligase (New England Biolabs, Inc.) in T4 DNA binding buffer, and electroporated in *E. coli* DH10b. The cloning of the gene was examined by miniprep with a plasmid spin kit (Genenmed).

For expression of a pET system, the cloned vector was transformed into expressed strain *E. coli* and examined again by miniprep. After the cloned *E. coli* strain had been grown overnight on a plate, one colony was inoculated into 5 ml of an LB amp broth and cultured until $OD_{600}$ reached about 1.0. 5 ml of the culture broth was added to 500 ml of a fresh LB amp broth, and cultured for 2 to 3 hours. When $OD_{600}$ reached 0.5 to 1.0, IPTG was added to the culture broth at 1 mM so as to induce the expression of protein. After the protein induction had been induced overnight at 20° C., the culture broth was centrifuged and the supernatant was discarded and only *E. coli* was collected. The subsequent protein purification was performed with a HIS BIND® purification kit (Novagen). The cell pellet was suspended in ⅕ volumes of buffer (0.1% TRITON™ X-100, t-Octylphenoxypolyethoxyethanol, 50 mM pH 8.0 Tris-HCl), and then 0.1 mg/ml of lysozyme (Sigma) was added to the suspension. The resulting suspension was sonicated so as to disrupt the *E. coli* cells. After centrifugation at 27000×g for 30 minutes, the supernatant was passed through an NTA-chelated agarose CL-6B (Peptron, Inc.) column which had been prepared by adding Ni ions into filling buffer. The protein-adsorbed column was treated with a 10-fold column volume of binding buffer (5 mM imidazole, 0.5M NaCl, 20 mM pH7.9 Tris-HCl) and a 6-fold volume of washing buffer (60 mM imidazole, 0.5M NaCl, 20 mM pH7.9 Tris-HCl) so as to remove non-specifically adsorbed proteins. Finally, the p60 protein bound to the column was isolated with elution buffer (1 mM imidazole, 0.5M NaCl, 20 mM pH7.9 Tris-HCl). The obtained p60 protein was examined by SDS-PAGE gel electrophoresis.

Example 2

Preparation of Hybridoma Cells 2-1: Antibody-Production Cells

The p60 protein prepared in Example 1 was electrophoresed on a SDS-PAGE (polyacrylamide gel electrophoresis) gel, and the gel fragment was cut, and then an emulsion containing the same volume of complete Freud's adjuvant was prepared. The emulsion was injected into the abdominal cavity of 5 seven-week-old female BALB/C mice. 20 μg of the antigen per one animal was injected in a total emulsion volume of 400 μl. After two weeks, an emulsion containing incomplete Freud's adjuvant was injected into the abdominal cavity of the mice, and after two weeks, 10 μg/mouse of the antigen dissolved in PBS was injected into the abdominal cavity of the mice so as to induce the production of an antibody. In order to examine whether the antibody had been produced or not, ELISA and Western blot assays were performed. Then, at 3 days before entering cell fusion, the antigen dissolved in PBS was injected again into the tail vein of the mice. To prevent contamination, all the mice were bred at a selected region.

2-2: Identification and Selection of Antigen-Production Cells

A blood sample was collected from the eyeballs of the mice immunized in the above manner and put in a 1.5-ml centrifugation tube. Serum was isolated from the blood sample by centrifugation (at 1800 rpm for 10 minutes) and stored at −20° C. before a test for the production of an antigen.

The antibody production was confirmed with the p60 protein by an ELISA assay, and then, fusion to cell-production cells was started. The p60 protein expressed in *E. coli* was coated on a 96-well plate at the amount of 0.5 μg/well and then allowed to react overnight. After washing three times with PBST (PBS buffer, 0.05% TWEEN® 20 (polyoxyethylene-20-Sorbitan monolaurate)), the reaction was terminated with 1% BSA. After washing three times with PBST again, the serum was diluted to 1:500-2000 followed by reaction for 1 hour. After washing three times with PBST, the resulting serum was treated with anti-mouse IgG-conjugated HRP and allowed to react for 1 hour. Next, after washing three times with PBST, each well was treated with 100 μl OPD (Sigma) and color-developed for 20 minutes. After addition of 15 μl of a reaction-terminating solution (8N sulfuric acid), the absorbance at 492 nm was measured.

2-3: Preparation of Hybridoma Cells

The mice determined to produce the antibody were sacrificed from which antibody-producing spleen cells were isolated. The isolated cells were fused with myeloma cell P3X63Ag8.653 according to a modified fusion method (Method in Enzymology, vol. 73, p3. Academic Press, New York) derived from a fusion method (Cesar Milstein and Georges Kohler's method).

The P3X63Ag8.653 cells of the mice were maintained to the optimum growth stage using 10% FBS RPMI1640 medium in a culture dish. At one day before cell fusion, the P3X63Ag8.653 cells were diluted to $3 \times 10^5$ cells/ml, and on the next day, 50 ml of the cell dilution was taken and centrifuged at 400×g for 3 minutes. The centrifuged cells were washed two times with serum-free medium and adjusted to a concentration of $1 \times 10^7$ cells/ml. Then, the mice were sacrificed by cervical dislocation, and the spleen was collected from the sacrificed mice and placed in a mesh container to isolate each cell. At this time, all the media were used in a serum-free state. The completely isolated antibody-producing cells were centrifuged at 400×g for 5 minutes, washed two times with serum-free medium, and then suspended in 10 ml of medium. Lymphocytes were counted with a haemocytomer, and $10^8$ lymphocytes were mixed with $1 \times 10^7$ P3X63Ag8.653 cells (10:1) and centrifuged at 400×g for 3 minutes. To the centrifuged cells, 1 ml of 50% PEG (Sigma) solution was added slowly over one minute. The resulting fusion cell solution was diluted at 4 ml/3 minutes, 5 ml/4 minutes, and then 20 ml/5 minutes, with RPMI 1640 medium. The cell dilution was centrifuged at 400×g for 3 minutes and suspended in 35 ml of HAT selection medium. 100 µl of the suspension was spread on a 96-well plate which had been coated with feeder cells (macrophages isolated from the abdominal cavity of mice with PBS) before one day. Then, the suspension was cultured in a 5% $CO_2$ incubator at 37° C. for 7-14 days.

2-4: Selection and Isolation of Hybridomas

The culture supernatant obtained in Example 2-3 was taken from which positive clones to the p60 protein were selected by a direct ELISA method. Then, Western blot test was performed to confirm that the selected clones are positive clones. From a number of the hybridomas, 10 hybridoma cells having a high antibody activity (OD of more than 1.2) to the p60 protein were obtained.

Such confirmed positive clones were diluted in a series of processes, and the fusion cells of the diluted clones were spread on a 96-well plate at 0.5 cells per each well, and cultured for 7 days and then assayed by ELISA and Western blotting. The final positive clones were verified, and antibodies p6007, p6013, p6017, p6030 and p6033 designated according to their natures and recognition sites were isolated from the final positive clones. The finally verified fusion cells were transferred to a 24-well plate, and then to well plates having gradually increasing well number, and finally transferred and cultured in a T25 flask.

Among the screened hybridomas producing the p60 protein antibody, hybridomas p6007 and p6017 were deposited with Korean Collection for Type Cultures (KCTC, Oun-dong, Yusong-gu, Daejeon, Korea) on Feb. 21, 2003 under accession numbers KCTC 10431BP and KCTC 10432BP, respectively.

Example 3

Antibody Production and Isolation

Using the positive clone according to each antibody obtained in Example 2, culture solutions in the mouse abdominal cavity were prepared from which antibodies were isolated. The preparation and isolation of the culture solutions were performed in the same manner for all the culture solutions except for hybridoma cells producing the respective antibodies.

In order to obtain the abdominal cavity culture solutions of the antibodies distinguished in Example 2, $3 \times 10^6$ cells of positive clones which produce the respective monoclonal antibodies confirmed by ELISA and Western blot assays were injected into the abdominal cavity of BALB/C mice which had been pre-treated with prestin before one week. After 10-15 days, 3-10 of ascites were extracted from the mice. Both the monoclonal antibodies p6007 and p6017 were prepared in the same manner except for the final verification step. In order to male each of the antibodies, abdominal cavity culture solutions containing the respective antibodies were independently obtained, from which the antibodies were isolated in the following manner.

The ascites obtained as described above were purified through a protein A affinity column (Amersham Bioscience, HITRAP™ rProtein A FF). Namely, the ascites were passed through the protein A column which had been homogenized with a 10-fold volume of DPBS at a rate of 1 ml/minute. At this time, the rate was maintained by an AKTA purifier (Amersham Bioscience), and the column was eluted with 100 mM glycine (pH 3.0) and then neutralized with a ¹⁄₁₀-fold amount of 2M Tris (pH 8.0). At this time, the elution rate was maintained at a rate of 1 ml/minute for the purification and isolation of each antibody.

Example 4

ELISA and Western Blot Tests Using Monoclonal Antibodies

The monoclonal antibodies p6007 and p6017 isolated in Example 3 were subjected to ELISA and Western blot tests, and whether such antibodies recognize the known peptides pepA (Ser-Thr-Pro-Val-Ala-Pro-Thr-Gln-Glu-Val-Lys-Lys) (SEQ ID NO:3) and pepD (Gln-Gln-Gln-Thr-Ala-Pro-Lys-Ala-Pro-Thr-Glu) (SEQ ID NO: 4) or not was observed.

The results of a direct ELISA assay using 100 ng of a polyclonal antibody as a capture antibody confirmed that the polyclonal antibody which detects all *Listeria* spp. except for one *Listeria grayi* among a total of 19 *Listeria* spp. can be used as a second antibody in sandwich ELISA for detecting *Listeria monocytogenes* (FIG. 1*a*). Furthermore, the results of Western blot assay for the polyclonal antibody showed that the polyclonal antibody detected all *Listeria* spp. except for *Listeria grayi* (FIG. 1*a*).

The results of a sandwich ELISA assay using 200 ng of the monoclonal antibody p6007 as a capture antibody and 100 ng of the polyclonal antibody as a second antibody indicated that 6 *Listeria* spp. except for *Listeria monocytogenes* among a total of 19 *Listeria* spp. had a blank OD value of about 0.3, and 13 *Listeria monocytogenes* had an OD level of more than 0.9. Such results suggest that the monoclonal antibody p6007 is suitable for the specific detection of *Listeria monocytogenes* (FIG. 1*b*). Furthermore, the results of a Western blot assay using the monoclonal antibody p6007 likewise showed that the monoclonal antibody p6007 detected only *Listeria monocytogenes* among *Listeria* spp. (FIG. 1*b*).

Moreover, sandwich ELISA analysis was performed using 200 ng of the monoclonal antibody p6017 detecting all *Listeria* spp. as a capture antibody and 100 ng of the polyclonal antibody as a second antibody, and the analysis results showed that the p6017 monoclonal antibody detected all *Listeria grayi, Listeria welshimeri, Listeria innocua, Listeria ivanovii, Listeria monocytogenes,* and *Listeria seeligeri* (FIG. 1*c*). Such results indicate that the monoclonal antibody p6017 is suitable as a second antibody for the monoclonal antibody p6007. Also, a Western blot assay using the monoclonal antibody p6017 was performed, and the results showed that the monoclonal antibody p6017 detected not only *Listeria monocytogenes* but also *Listeria ivanovii*, indicating that it is suitable as a second antibody for the monoclonal antibody (FIG. 1*c*).

Furthermore, direct ELISA analysis using 100 ng of the polyclonal antibody as a capture antibody was performed for a total of 33 *Listeria monocytogenes* strains isolated from food, and the results showed that the polyclonal antibody detected all of the 33 *Listeria monocytogenes* strains, thus indicating that, in the same manner as in FIG. 1*a*, the polyclonal antibody can be used as a second antibody in sandwich ELISA for detecting *Listeria monocytogenes* (FIG. 2a). In addition, the results of Western blot analysis using the polyclonal antibody likewise showed that the polyclonal antibody detected all the *Listeria monocytogenes* strains (FIG. 2a).

Furthermore, using 200 ng of p6007 as a capture antibody and 100 ng of p6017 as a second antibody, a total of 33 *Listeria monocytogenes* strains isolated from food were cultured in BHI broth overnight at 37° C., and centrifuged at 3000 rpm for 15 minutes, and the supernatant was treated in boiling water for 10 minutes. The resulting bacterial solution was inoculated at 100 µl/well and subjected to sandwich ELISA analysis. The results indicated that the monoclonal antibodies were positive to all the food strains and showed 100% sensitivity and specificity (FIGS. 2b and 2c). Such data confirms the characteristic abilities of p6007 and p6017 again.

Furthermore, in order to examine the affinity or difference between the monoclonal antibodies p6007 and p6017, binding dynamic quantification by Western blot and image analysis was performed. As shown in FIG. 6a, the p6007 monoclonal antibody easily detected even a small amount of 5 ng of *Listeria monocytogenes* p60, whereas *Listeria innocua* p60 could be detected only at the case of addition of more than 50 ng. After the addition of 50 ng, the comparison between the combined concentrations of *Listeria monocytogenes* p60 and *Listeria innocua* p60 shows a 100 times difference. On the other hand, as shown in FIG. 6b, there is no great difference in the effect of p6017 between *Listeria monocytogenes* p60 and *Listeria innocua* p60. Such data indicate that p6007 at a typical concentration of a culture supernatant can distinguish *Listeria* spp. p60 different from *Listeria monocytogenes* p60.

Meanwhile, whether the monoclonal antibodies p6007 and p6017 recognize pepA and pepD or not was examined by direct ELISA method. As coating antigens, 100 ng of recombinant *Listeria monocytogenes* p60, 100 ng of recombinant *Listeria innocua* p60, 500 ng of pepA, 500 ng of pepD, and 500 ng of a negative control peptide, were used, and as capture antibodies, 500 ng of a polyclonal antibody, 500 ng of monoclonal antibody p6007, and 500 ng of monoclonal antibody p6017, were used. As shown in FIG. 4a, the examination results showed that only the polyclonal antibody was conjugated to pepA, and both the monoclonal antibodies p6007 and p6017 were not conjugated to pepA and pepD, thus indicating that the monoclonal antibodies do not use the epitopes of pepA and pepD.

Furthermore, the competition between pepA and pepD was assayed by sandwich ELISA using 200 ng of the monoclonal antibody p6007 as a capture antibody, and 100 ng of *Listeria monocytogenes* as a sample. In the case of FIG. 4b, a polyclonal antibody was used as a second antibody, and at the same time, 1 µg-1 ng of each of pepA and pepD were added as a negative control peptide, and peptide Gly Asn Thr Phe Ser Leu Glu Glu Val Asp Lys Leu Gly Cys Arg Asp Thr Arg Leu Leu (SEQ ID NO: 5) was used as a control peptide. In the case of FIG. 4c, 1 µg-1 ng of each of pepA and pepD was added as a negative control peptide to the biotinylated monoclonal antibody p6017, and peptide Gly Asn Thr Phe Ser Leu Glu Glu Val Asp Lys Leu Gly Cys Arg Asp Thr Arg Leu Leu (SEQ ID NO: 5) was used as a control peptide. As shown in FIGS. 4b and 4c, the assay results showed that the monoclonal antibody p6007 had saturated OD values without a difference in OD values with a change in the addition amounts of pepA and pepD, even though OD values must be changed with a change in the addition amounts of pepA and pepD if the monoclonal antibody p6007 utilizes the epitopes of pepA and pepD. This suggests that the monoclonal antibody p6007 do not utilize the epitopes of pepA and pepD, in the same manner as in FIG. 4a. As a result, it is believed that, when applied to a sandwich ELISA kit, the monoclonal antibodies p6007 and p6017, and the polyclonal antibody, do not use pepA and pepD as epitopes.

Example 5

ELISA Kit for Detecting *Listeria monocytogenes*

To prepare an ELISA assay kit for detecting *Listeria monocytogenes*, the p6007 monoclonal antibody specific to *Listeria monocytogenes* and the p6017 monoclonal antibody specific to *Listeria* spp. were used.

Concretely, the following test was performed.

The purified p6007 monoclonal antibody as a capture antibody was diluted in 50 mM carbonate buffer (pH 9.6) to 5 µg/ml, and 100 µl of the dilution was spread on a 96-well plate at 0.5 µg/well and allowed to react overnight at 4° C. The reaction solution was discarded and each well was washed three times with PBS containing 0.05% TWEEN® 20.

In order to block the empty space of the plate, 200 µl of PBS containing 0.05% TWEEN® 20 and 1% BSA was put in each well, allowed to react at 37° C. for one hour, and each well was washed three times.

A sample was prepared by growing *Listeria* spp. in *Listeria* growth medium overnight, centrifuging 1 ml of the culture medium at 3000 rpm for 10 minutes, and boiling the supernatant 10 minutes. 100 µl of the prepared sample was added to each well of the blocked plate. To evaluate the test effectiveness, the positive control and the negative control were also used. The plate was allowed to react at 37° C. for one hour. The reaction solution was discarded and each well was washed three times.

The monoclonal antibody p6017 as a second antibody was 0.1% BSA-containing PBS at 1 µg/ml, 100 µg of the dilution was placed into each well and allowed to react at 37° C. for one hour. After completion of the reaction, each well was washed three times.

The absorbance of the plate was measured. If the positive control showed an OD of 1.5-2.0 and the negative control showed an OD of less than 0.1, the reaction was regarded normal. If the sample showed an OD of 1.5, it seemed positive, and thus the bacteria of *Listeria monocytogenes* were isolated and identified. If the sample showed an OD of less than 0.1, it seemed negative, thus considering that the sample was not contaminated with *Listeria monocytogenes*.

The results of sandwich ELISA using varying amounts of the capture monoclonal antibody are shown in FIG. 3a. Concretely, FIG. 3a shows the results of sandwich ELISA performed using varying amounts of 200 ng, 500 ng, 1 µg and 2 µg of the monoclonal antibody p6007 as a capture antibody. In this case, as a second antibody, 100 ng of the biotinylated monoclonal antibody p6017 was used under reaction condition (detection marker: streptavidin-HRP). Since the monoclonal antibody p6007 which selectively recognizes *Listeria monocytogenes* was used as a capture antibody, only *Listeria monocytogenes* were detected and an increase in the amount of the monoclonal antibody p6007 resulted in an increase in OD value. In the results, high OD value was shown when the capture antibody p6007 was used at the amount of 500 ng-2 µg in the sandwich ELISA kit.

The monoclonal antibody p6007 confirmed to selectively recognize only *Listeria monocytogenes* did not recognize other strains than the *Listeria* strains, i.e., *Eschericia*, *Entero-* coccus, *Enterobacter, Klebsiella, Pseudomonas, Staphylococcus, Streptococcus, Vibrio* and *Salmonella* strains (FIG. 3b).

Example 6

Rapid Diagnosis of *Listeria monocytogenes* Using Immunochromatography

In order to prepare dipsticks using immonochromatography for the rapid screening of *Listeria monocytogenes* which are important bacteria causing food poisoning, the monoclonal antibody p6007 was conjugated to colloidal gold (40 nm), the monoclonal antibody p6017 was used as a capture antibody, and anti-mouse IgG was used as a control antibody. If a band was produced at a control line, the test was considered effective. If bands were produced at both a control line and a capture line, it was considered positive, and thus *Listeria monocytogenes* bacteria were isolated and identified. If a band was produced only at a control line, it was considered negative, thus determining that there were no *Listeria monocytogenes*.

Concretely, the results of application of recombinant *Listeria monocytogenes* p60 as a sample are shown in FIG. 5a. In FIG. 5a, strips 1 to 7 represent the results of use of p60 at the amounts of 1000 ng, 500 ng, 250 ng, 125 ng, 60 ng, 30 ng, and 15 ng, respectively, and strip 8 represents a negative control. Meanwhile, FIG. 5b shows the results of application of *Listeria monocytogenes* in place of p60 as a negative control (strip 0) and application of culture supernatants of various strains (strips 1 to 12). In FIG. 5b, the strips 1 to 12 were for *Streptococcus pyogenes, Shigella flexneri, Staphylococcus aureus, Pseudonomas aeruginosa, Klebsiella pneumoniae, Enterococcus faecalis, Escherichia coli, Enterobacter aerogenes, Vibrio parahaemolyticus, Vibrio cholerae, Staphylococcus epidermidis, Salmonella typhi*, respectively.

The recombinant p60 and the culture supernatants of *Listeria monocytogenes* showed a band at a capture line, but the supernatant of the negative control did not show any band at a capture line. As a result, it was confirmed that the dipsticks prepared as described above could selectively recognize only p60.

Such results suggest that a pair of the monoclonal antibodies p6007 and p6017 can be advantageously applied for dipsticks selectively recognizing *Listeria monocytogenes* p60.

Test methods used in Examples are as follows.

Test Example 1

Sandwich ELISA Test

1. The monoclonal antibody (p6007 or p6017) which selectively recognizes *Listeria monocytogenes* was plated on each well at 100 ng/100 μl and incubated at 37° C. for 2 hours.

2. Each well was washed three times with 0.05% TWEEN® 20-containing PBS solution.

3. 100 μl of 1% BSA was plated on each well and incubated at 37° C. for one hour so as to block each well.

4. Each well was washed three times with 0.05% TWEEN® 20-containing PBS solution.

5. 100 μl of an antigen was plated on each well and incubated at 37° C. for one hour. Concretely, for blanks, 0.1% BSA was spread, and for a positive control, recombinant *Listeria monocytogenes* p60 was plated at the amount of 100 ng/well. For a test strain, it was cultured in 5 ml of BHI (brain hert infusion; DIFCO Co.) broth at 37° C. for 18 hours, and then the BHI broth was centrifuged at 3000 rpm for 15 minutes, and the supernatant was spread on each well.

6. Each well was washed three times with 0.05% TWEEN® 20-containing PBS solution.

7. A polyclonal antibody (rabbit) or a monoclonal antibody was plated on each well at the amount of 100 ng/100 μl and incubated at 37° C. for one hour.

8. A HRP (horse radish peroxidase)-conjugated anti-rabbit antibody (diluted with PBST at 1:1000) was plated on each well at the amount of 100 ng/100 μl and incubated at 37° C. for one hour.

9. Each well was washed with three times with 0.05% TWEEN® 20-containing PBS solution.

10. A color-development reagent was prepared by 9.45 ml of color-development buffer solution as described below, 0.5 ml of 4% OPD (o-phenylene diamine) and 0.05 ml of $H_2O_2$, and 100 μl of the color-development reagent was plated on each well and incubated at ambient temperature for 20 minutes.

| Color-development buffer solution | |
|---|---|
| Name | Addition amount |
| Citric acid (monohydrate) | 3.66 g |
| Potassium phosphate ($K_2PO_4$) | 11.35 g |
| D.W. | 1000 ml |

11. 15 μl of termination solution 8N $H_2SO_4$ was placed on each well.

12. The OD value at 492 nm was measured.

Test Example 2

Direct ELISA Test 1. 100 μl of an antigen was plated on each well and incubated at 37° C. for 2 hours.

2. Each well was washed three times with 0.05% TWEEN® 20-containing PBS solution.

3. 100 μl of 1% BSA was placed on each well and incubated at 37° C. for 1 hour.

4. Each well was washed three times with 0.05% TWEEN® 20-containing PBS solution.

5. 100 μl of an antibody or 1% BSA (blank) was plated on each well and incubated at 37° C. for 1 hour.

6. 100 μl of a HRP-conjugated anti-mouse antibody or a HRP-conjugated anti-rabbit antibody (diluted with PBST at 1:10,000) was plated on each well and incubated at 37° C. for one hour.

7. A color-development reagent obtained by mixing 9.45 ml of color-development buffer solution as described below, 0.5 ml of 4% OPD (o-phenylene diamine) and 0.5 ml of $H_2O_2$ was placed on each well and incubated at ambient temperature for 20 minutes.

| Color-development buffer solution | |
|---|---|
| Name | Addition amount |
| Citric acid (monohydrate) | 3.66 g |
| Potassium phosphate ($K_2PO_4$) | 11.35 g |
| D.W. | 1000 ml |

15 μl of termination solution 8N $H_2SO_4$ was placed on each well.

12. The OD value at 492 nm was measured.

Test Example 3

Western Blot Test 1. 250 μl of a supernatant obtained by culturing *Listeria* spp. in BHI broth at 37° C. overnight was well mixed with 50 μl of a sample buffer (×6) containing brilliant blue R as a dye, and immersed in boiling water, and 20 μl of the mixture was taken and loaded onto 12% sulfate-polyacrylate gel electrophoresis (SDS-PAGE) gel.
2. After completion of the electrophoresis, the sample was transferred to an NC (nitrocellulose) membrane at 4° C. overnight.
3. The membrane was washed with 0.05% TWEEN® 20-containing PBS solution.
4. The membrane was blocked with 5% skimmed milk at ambient temperature for 1 hour.
5. The membrane was washed with 0.05% TWEEN® 20-containing PBS solution.
6. The nitrocellulose membrane was immersed in a mixture solution of 10 ml of 5% skimmed milk and 10 μl of an antibody at ambient temperature for 1 hour.
7. The membrane was washed with 0.05% TWEEN® 20-containing PBS solution.
8. The nitrocellulose membrane was immersed in 10 ml of a HRP-conjugated anti-mouse antibody or a HRP-conjugated anti-rabbit antibody (diluted with 5% skimmed milk at 1:10,000) at ambient temperature for one hour.
9. The membrane was incubated with SUPERSIGNAL® WestPico Chemiluminescent Substrate (PIERCE lit), and the light emission was measured with a chemiluminescence meter.

Example 4

Dipstick Test

1. The optimum concentration of the p6007 monoclonal antibody to be conjugated to gold particle (40 nm) was determined and then a suitable concentration of the monoclonal antibody was added to colloidal gold and allowed to react for 30 minutes at room temperature with rotation. After 30 minutes, BSA was added to the reaction mixture and allowed to react at 4° C. overnight. The reaction mixture was centrifuged at 4° C. and 10000 rpm for one hour, and the supernatant was carefully discarded, and the gold pellet was suspended at about 1/10 of the initial volume. The resulting p6007 monoclonal antibody-conjugate gold particle was adjusted at an absorbance of 1 at 420 nm, and injected onto a bonding pad. The resulting bonding pad was dried at 60° C. for one hour under vacuum. After drying, the bonding pad was stored at a relative humidity (RH) of less than 30% until use.
2. A nitrocellulose membrane was treated with a capture antibody and a control antibody. As the capture antibody, the monoclonal antibody p6007 specific to *Listeria* spp. was spread at the amount of 1 μg per cm of the nitrocellulose membrane. As the control antibody, 1 mg/ml of anti-mouse IgG was spread at the amount of 1 μg per ml of the nitrocellulose membrane. The treated membrane was dried at 37° C. overnight and stored at a relative humidity (RH) of less than 30%.
3. A sample pad was blocked with a suitable buffer solution so as to make a sample suitable for application. The sample pad was dried at 60° C. for one hour, and then stored at a relative humidity (RH) of less than 30% until use.
4. The pads prepared as described above were linked to the bonding pad and then used in sample screening.
5. *Listeria* bacteria were grown in *Listeria* growth medium, and 1 ml of the culture medium was taken and centrifuged at 3000 rpm for 10 minutes, and the supernatant was boiled for 10 minutes for use as a sample.
6. 100 μl of the sample prepared as described above was dropped onto the sample pad, and after 5 minutes, was read.

As described above, the inventive monoclonal antibody p6007 selectively recognizes only *Listeria monocytogenes*, so that the use of such an antibody allows for rapid determination of the food contamination with these bacteria pathogenic to humans.

---

What is claimed is:

1. A monoclonal antibody binding specifically to the p60 protein of *Listeria monocytogenes*, the monoclonal antibody being produced by a hybridoma cell of accession number KCTC 10431BP.

2. A hybridoma cell KCTC 10431BP which produces the monoclonal antibody as claimed in claim 1.

3. A method for detecting *Listeria monocytogenes* contamination, which comprises: contacting the monoclonal antibody of claim 1 with a test sample comprising a p60 protein of *Listeria monocytogenes*, and determining the presence of an antigen-antibody complex between the p60 protein of *Listeria monocytogenes* and the monoclonal antibody.

4. The method of claim 3, wherein the antigen-antibody complex is detected by an RIA, ELISA, immunofluorescence, particle agglutination or chemiluminescence assay.

5. The method of claim 3, wherein a monoclonal antibody produced by a hybridoma cell of accession number HCTC 1043BP that binds specifically to the p60 protein of *Listeria* species binds to the antigen of the antigen-antibody complex.

6. A kit for claims detecting *Listeria monocytogenes* contamination comprising the monoclonal antibody of claim 1.

7. The kit of claim 6, wherein the kit comprises a dipstick kit for immunochromatography.

8. The kit of claim 6, further comprising a monoclonal antibody produced by a hybridoma cell of accession number KCTC 10432BP that binds specifically to the p60 protein of *Listeria* spp.

* * * * *

UNITED STATES PATENT AND TRADEMARK OFFICE
CERTIFICATE OF CORRECTION

PATENT NO. : 7,390,489 B2  Page 1 of 1
APPLICATION NO. : 10/961274
DATED : June 24, 2008
INVENTOR(S) : Byung Soo Youn et al.

It is certified that error appears in the above-identified patent and that said Letters Patent is hereby corrected as shown below:

| Error Location In Issued Patent | | Description of Error and Correction |
|---|---|---|
| Column | Line | |
| Title Page | Item (73), Assignee | delete "Komed Co., Ltd. (KR)" and insert therefor -- AdipoGen, Inc., Republic of Korea --. |
| In Drawing Sheet 5 of 8 (Y-axis) (figure 3b) | 1 | Delete "V. cholarae" and insert -- V. cholerae --, therefor. |
| 2 | 20 | Delete "produce" and insert -- produced --, therefor. |
| 4 | 9 | Delete "hybriddoma." and insert -- hybridoma. --, therefor. |
| 7 | 26 | After "minutes" insert -- at --. |
| 9 | 66 | Delete "male" and insert -- make --, therefor. |
| 12 | 67 | Delete "Eschericia," and insert -- Escherichia, --, therefor. |
| 13 | 9-10 | Delete "immonochromatography" and insert -- immunochromatography --, therefor. |
| 13 | 31 | Delete "Pseudonomas" and insert -- Pseudomonas --, therefor. |
| 13 | 63 | Delete "hert" and insert -- heart --, therefor. |
| 18 | 45 | In Claim 6, after "for" delete "claims". |

Signed and Sealed this

Twenty-sixth Day of May, 2009

JOHN DOLL
*Acting Director of the United States Patent and Trademark Office*

SEQUENCE LISTING

```
<160> NUMBER OF SEQ ID NOS: 5

<210> SEQ ID NO 1
<211> LENGTH: 35
<212> TYPE: DNA
<213> ORGANISM: Artificial
<220> FEATURE:
<223> OTHER INFORMATION: primer

<400> SEQUENCE: 1
gggaattcca tatgagcact gtagtagtcg aagct                     35

<210> SEQ ID NO 2
<211> LENGTH: 28
<212> TYPE: DNA
<213> ORGANISM: Artificial
<220> FEATURE:
<223> OTHER INFORMATION: primer

<400> SEQUENCE: 2
gccgctcgag tacgcgaccg aagccaac                             28
```

```
<210> SEQ ID NO 3
<211> LENGTH: 12
<212> TYPE: PRT
<213> ORGANISM: Listeria monocytogenes
<220> FEATURE:
<221> NAME/KEY: PEPTIDE
<222> LOCATION: (1)..(12)
<223> OTHER INFORMATION: pepA

<400> SEQUENCE: 3

Ser Thr Pro Val Ala Pro Thr Gln Glu Val Lys Lys
1               5                   10

<210> SEQ ID NO 4
<211> LENGTH: 11
<212> TYPE: PRT
<213> ORGANISM: Listeria monocytogenes
<220> FEATURE:
<221> NAME/KEY: PEPTIDE
<222> LOCATION: (1)..(11)
<223> OTHER INFORMATION: pepD

<400> SEQUENCE: 4

Gln Gln Gln Thr Ala Pro Lys Ala Pro Thr Glu
1               5                   10

<210> SEQ ID NO 5
<211> LENGTH: 20
<212> TYPE: PRT
<213> ORGANISM: Artificial
<220> FEATURE:
<223> OTHER INFORMATION: control peptide

<400> SEQUENCE: 5

Gly Asn Thr Phe Ser Leu Glu Glu Val Asp Lys Leu Gly Cys Arg Asp
1               5                   10                  15

Thr Arg Leu Leu
            20
```